United States Patent [19]

Caslavsky et al.

[11] Patent Number: 4,563,351

[45] Date of Patent: Jan. 7, 1986

[54] SELF-GELLING THERAPEUTIC COMPOSITIONS FOR TOPICAL APPLICATION

[75] Inventors: Vera B. Caslavsky, Lexington, Mass.; Poul Gron, Salem, N.H.

[73] Assignee: Forsyth Dental Infirmary for Children, Boston, Mass.

[21] Appl. No.: 617,977

[22] Filed: Jun. 6, 1984

Related U.S. Application Data

[60] Continuation of Ser. No. 518,951, Aug. 1, 1983, which is a division of Ser. No. 381,530, May 24, 1982, Pat. No. 4,411,889.

[51] Int. Cl.$^4$ .............................................. A61K 33/16
[52] U.S. Cl. ....................................... 424/151; 424/52
[58] Field of Search .................................. 424/151, 52

[56] References Cited

U.S. PATENT DOCUMENTS 4,411,889 10/1983 Caslavsky et al. ................. 424/151

Primary Examiner—Shep K. Rose
Attorney, Agent, or Firm—Richard P. Crowley

[57] ABSTRACT

A self-gelling aqueous therapeutic composition for topical application and for the sustained release of a medicant compound, which compositions comprise an aqueous ethyl orthosilicate emulsion, a therapeutic compound which is to be released in a sustained manner on topical application, a gelling facilitating agent to aid the in situ gelation of the ethyl orthosilicate composition comprising a surface-active agent and/or a low concentration of an ammonium or fluoride compound and a gelling accelerating compound to accelerate the conversion of the solution to a gel state, which accelerator compound comprises an imidazole compound to effect the self gelling of the composition.

21 Claims, No Drawings

SELF-GELLING THERAPEUTIC COMPOSITIONS FOR TOPICAL APPLICATION

REFERENCE TO GOVERNMENT SUPPORT

Some portions of the disclosure and examples of this application were supported by Grant No. De5067 from the National Institute of Dental Research, a division of the United States National Institute of Health.

REFERENCE TO PRIOR APPLICATION

This application is a continuation-in-part of U.S. patent application Ser. No. 518,951, filed Aug. 1, 1983 (hereby incorporated by reference in its entirety), which application is a divisional application of U.S. patent application Ser. No. 381,530, filed May 24, 1982, now U.S. Pat. No. 4,411,889, issued Oct. 25, 1983, which patent is hereby incorporated by reference in its entirety.

BACKGROUND OF THE INVENTION

U.S. Pat. No. 4,411,889 discloses a system of topical fluoride treatment in the oral cavity which combines the advantages of an application of a solution with those of a gel. The patent describes a fluoride-containing, self-gelling aqueous composition for topical application on tooth surfaces in the oral cavity for the prevention of dental caries. The self-gelling composition comprises a low-viscosity liquid aqueous composition of a monomer or prepolymer of an alkyl such as ethyl orthosilicate (also known as tetraethoxy silane (TES)), a water-soluble fluoride compound to inhibit or prevent dental caries and a gelation agent, such as a fluoride compound and a surface-active agent to provide for the in situ gelation of the composition from a low-viscosity liquid composition to a gelled state. Typically the gelation occurs from a liquid to a gel state in a time period of about one hour or less after mixing through the hydrolysis of the orthosilicate. The self-gelling transformation at a neutral pH is favored by high concentration of the fluoride, which acts both as a caries preventative agent and as a gelation facilitating agent, ammonium ions, intensified emulsification and temperature increase. The self-gelling composition usefully employs a variety of surface-active agents such as those agents, such as sodium lauryl sulfate, cetylpyridinium halides, and nonionic agents, such as the polyoxyethylene derivatives of fatty acid esters of sorbitol anhydrides. Optionally, the self-gelling compositions may include buffering agents, viscosity increasing agents, while preferred compositions employ a water soluble fluoride in combination with a surface-active agent.

U.S. Pat. No. 4,411,889 and the co-pending application Ser. No. 518,951 also describes the employment of various drug compounds in place of the fluoride dental caries preventative agent, so as to provide for a self-gelling composition for the sustained release of the drug compound. The self-gelling, drug-containing aqueous system is typically used for topical applications, both in the oral cavity; for example, in periodontal pockets, as well as for human and veterinary use, such as for the treatment of mastitis by the application of a topical coating to the affected area. The self-gelling composition provides for the sustained release of an antibiotic, antibacterial or other therapeutic drug compound. The self-gelling aqueous composition typically comprises, but is not limited to, an emulsion of the ethyl orthosilicate as a monomer or prepolymer in an amount of about 5 to 30 percent by weight, drug compound selected for its therapeutic effect which may or may not be water soluble and a gelling facilitating agent, typically a surface-active agent, generally in an amount of from about 0.01 to 2 percent by weight of the composition. The composition is a low viscosity liquid system generally having a pH of 3 to about 8.5 and typically 6 to 7, which after vigorous mixing and on topical application changes the state from a liquid to a gel in a time period from about 1 hour or less.

It is desirable to provide for a self-gelling liquid composition which contains a wide variety of therapeutic compounds for topical application and which has accelerated gelling time.

SUMMARY OF THE INVENTION

The invention relates to improved self-gelling compositions containing therapeutic compounds and to a method of preparing and using such compositions. The invention concerns self-gelling liquid compositions for the sustained release of therapeutic compounds in which the conversion of the compounds from a liquid to a gel is accelerated by the employment of accelerating agents and to a method of preparing and using such improved self-gelling accelerated compositions.

An improved self-gelling liquid composition has been discovered to provide, dissolve, or disperse therapeutic compounds, such as a drug or medication or other compound designed to have a therapeutic affect to a particular application site, such as for animals or humans and then to gel in situ within a short controlled period of time to provide for the sustained release of the therapeutic compound from the gel composition to the site. The accelerated self-gelling compositions of the invention typically comprise a low-viscosity liquid aqueous emulsion of a monomer or a prepolymer of alkyl orthosilicate, more particularly an ethyl orthosilicate in an amount to provide for the conversion of the liquid to a gel state on hydrolysis of the orthosilicate and a gelling facilitating agent in an amount to provide for the in situ gelation of the low-viscosity liquid after topical application to a gel state or condition. Gelling facilitating agents suitable for use include low concentration amounts of fluoride compounds where the fluoride acts as a gel conversion facilitator rather than as a therapeutic or dental caries preventative agent, an ammonium compound, and/or a variety of effective surface-active agents.

The self-gelling composition also includes a therapeutic compound which is to be released in order to treat the conditions on the application site for which the therapeutic compound is selected and applied. A wide variety of therapeutic compounds may be employed, alone or in combination, based on the desired therapeutic affects. The therapeutic compounds may be water soluble or may merely be dispersed in the self-gelling aqueous composition.

The present invention is particularly concerned with an improved self-gelling composition wherein an accelerating compound is incorporated into the self-gelling aqueous composition in order to provide for an acceleration of the conversion time of the liquid solution to a gel state. A variety of selected accelerating compounds have been discovered for use in the self-gelling composition to provide for the controlled conversion of the composition from the liquid to the gel state and which compounds provide for effective acceleration of the gelation time to a short period of time, such as less than 10 minutes and typically less than 5 or more particularly between 0 and 3 minutes.

One particular class of accelerating compounds comprises a basic 5 or 6 membered nitrogen-containing heterocyclic compound, such as for example, imidazole or the alkyl imidazoles, such as methyl imidazole and the salts thereof, which have been found to be particularly effective, especially when the gelling agent comprises a low concentration amount of a fluoride in combination with a surface-active agent. The concentration of the various components of the self-gelling composition may be varied as desired in order to provide for some change in the kinetics of gelation, the quality of the gel, and the degree of coagulation. If desired, the self-gelling composition may contain other additive agents, such as viscosity index improvers, buffering agents, color and sweetening agents, emollient-type agents, such as glycols, and other agents used in therapeutic compositions which do not affect the acceleration and sustained release of the therapeutic compound or the action of the self-gelling composition.

An accelerated, self-gelling aqueous composition would comprise, for example from about 10 to about 30 percent by weight of the composition of tetraethoxy silane as a monomer or its prepolymer, for example from about 10 to 1000 parts per million of a soluble fluoride compound, such as for example, an alkali fluoride, such as sodium or potassium fluoride or ammonium fluoride, from about 0 to about 10 percent of a surface-active agent which with the fluoride compound acts as a gelling facilitating agent, a therapeutic or medicant compound dissolved or dispersed in the composition above or below its saturation point, the compound selected for the particular therapeutic purpose for which sustained release is desired and from about 0.1 to 2 percent by weight of an imidazole accelerating compound, the acid salts thereof, such as imidazole-HCl, such as a methyl imidazole. Typically, such accelerated compositions have gelling times generally of less than about 3 minutes or less at about a room temperature of 70° to 75° F. after approximately 30 seconds to 2 minutes of vigorous mixing; for example, with a static mixer. It has been discovered that various factors favor the rapid conversion of the liquid to the gel, such as increasing the ethyl orthosilicate concentration, increasing the fluoride concentration, the presence of selected surface-active agents, the use of ammonium rather than sodium, potassium or rubidium salts, increasing the temperature in the range from 20° to 37° C. and the intensity of mixing. In the past, in order to achieve conversion from a liquid to a gel within a few minutes time, a relatively high concentration of a gelling facilitating agent, such as a fluoride solution with or without surface-active agents is to be employed.

It has been discovered that the conversion time from a liquid to a gel state of self-gelling, therapeutic-type aqueous compositions may be accelerated by the employment of accelerating agents and additives which comprise nitrogen-containing compounds and typically nitrogen containing heterocyclic compounds of 5 or 6 membered rings, 3, 4, 5, and 6 membered rings and more particularly unsaturated 5 and 6 membered heterocyclic ring compounds. Typical nitrogen containing-compounds include, but are not limited to, imidazoles, pyrrolines, pyridines, tetrazoles, triazoles. Similar heterocyclic compounds and their various derivatives; for example, methyl, hydroxyl, aldehydric, carbonyl, and other substituent groups and the salts thereof. Particularly useful as accelerating agents are imidazole and the lower alkyl, such as the mono and di methyl imidazole and hydroxy imidazole and the imidazole acid salts, such as the hydrochloric acid salts thereof. Although the nature of the ion employed may be varied as desired typically as a pharmaceutically accepted ion. The most preferred compounds would include 1h imidazole-HCl and 1 methyl imidazole, 4 methyl imidazole.

The amount of the accelerating agent may vary; for example, up to 5 weight percent of the self-gelling composition, but more typically ranges from about 0.1 to 2 weight percent, such as for example, from about 0.1 to 1 percent. Generally the amount of the accelerating agent to be employed affects the time desired between the conversion of the liquid to the gel state in the particular composition. Generally for work in the oral cavity; that is for dental use, the time of conversion should be less than about 10 minutes; for example, less than about 3 minutes; for example, about 30 seconds to 1 to 2 minutes permits the dentist to mix the product and to apply it to the desired area prior to gelation and not so long as to acquire an inordinant period of time for the patient to wait.

The accelerating compounds of the invention provide that the time of conversion between the liquid and the gel may be varied as desired depending upon the typical application and the wait possible. Thus, the accelerating compositions may be employed for converting the liquid to a gel at any time desired, but generally is less than 1 hour, more generally less than 10 minutes. The gelation time does vary with the amount and concentration of the gelling agent particularly the fluoride concentration and since it is desirable except where fluoride is to be employed as a dental caries preventative agent for other therapeutic affects to maintain a low level of fluoride composition. The gelation time increases with the decrease in concentration of the fluoride in the self-gelling concentration. In addition, there is some increase of the gelation time with the pH which is generally neutral or a self-gelling composition is desired between about pH 6 to 8, such as to about 7.

The invention relates to any self-gelling antibiotic or antibacterial-agent-containing or therapeutic compound-containing composition for use; for example, in the oral cavity in the treatment of oral diseases, particularly periodontal disease, or on topical application to the skin or in a body cavity by the sustained release of the agents after topical application or on topical application.

The composition of the invention comprises a low-viscosity, aqueous composition adapted to be converted, after mixing and topical application, from a liquid to a gel state. The self-gelling composition comprises an ingredient which undergoes a reaction, such as hydrolysis, with the formation of nontoxic polymer which converts the solution into a gel state. A typical material would include a silica acid ester monomer or prepolymer which, on hydrolysis, forms fine silica polymers and an alkyl alcohol. The composition also includes one or more active ingredients which are to be used at the site of topical application, and for which active ingredients sustained release is desired at the location from the gel. The composition also includes one or more gelling facilitating agents, such as gel catalysts, to convert the monomer or prepolymer orthosilicate into a gel state in a predetermined time period. Typically, the gelling facilitating agents may comprise fluoride ions, ammonium ions and surface-active agents, or combinations thereof. In some instances, the gelling agents, such as the fluoride and ammonium ion, may also act as the active therapeutic ingredient in the composition, such as the use of ammonium fluoride, sodium fluoride, or potassium fluoride as dental caries preventative agents.

The self-gelling composition is suitable for use on mucous membranes or on the skin and in the oral cavity, particularly for application if dental-caries-preventative or antibiotic agents are to be applied to the tooth surface or an active drug ingredient is to be applied for the treatment of periodontal disease. The self-gelling liquid composition, which readily enters cavities or spaces, may be applied topically to the tooth surface, periodontal pockets or other body locations or cavities on humans or animals, where in situ gelation is desired for the sustained release of the active ingredients.

The composition and technique of the invention permit the advantage of a low-viscosity liquid which more readily penetrates and enters into and fills the narrow spaces, for example, between the teeth or periodontal pockets and into narrow cavities or which may be applied directly to other body cavities or openings where the composition contains a drug, and permits the easy application of a liquid to any substrate, such as by the use of a topical applicator, spraying, injecting, coating, swabbing or other techniques. The composition provides the advantage of gelling in situ at a predetermined time, so that the newly formed gel state will conform to the space and location of topical application and not be rinsed or washed away easily. A further advantage is that, on conversion to the gel state, the active ingredient is slowly released; that is, there is sustained release of the incorporated active agent, to provide for improved delivery of the agent to the particular site of topical application. The composition and technique have significant advantages over currently available compositions which are solutions, gels or ointments, and which compositions do not change their viscosity after application and, therefore, incorporate both the advantages and disadvantages of the initial state of the composition. The self-gelling composition combines the initial easy and rapid distribution and penetration properties of a solution with the slow release and retention properties of a gel.

This invention is concerned with a self-gelling composition for use in the oral cavity, wherein an active ingredient, such as a fluoride-containing compound, or combination is used. The use of a low-viscosity liquid composition allows greater penetration into deep sulci in a given period of time on topical application. On conversion to the gel state, the active fluoride and drug has a reduced tendency to wash away from the tooth surface and the pockets, and, therefore, would have a prolonged or sustained reaction time with the enamel, enabling the enamel to take up more of the fluoride and the drug to act as a medication at the site.

The invention concerns a self-gelling composition containing antibacterial agents, such as antibiotics, alone or in combination with fluoride and ammonium-containing compounds, for use in the oral cavity and on mucous membranes. These compositions permit the penetration of the agent into periodontal pockets and the retention and slow release of the agents in the pockets, after conversion to the gel state.

The active material or therapeutic compound employed in the accelerated self-gelling composition may vary and include both water soluble and water insoluble compounds and their pharmaceutically-acceptable salts, alone or in combination, which are selected for therapeutic effects on humans and animals. Such therapeutic agents comprise medicants, drugs, steroids, hormones, chemotherapeutic agents and other compounds and may include, but not limited to: chlorhexidine, tetracycline, penicillin V-K salt, bacitracin, polymyxin B-sulfate, kanamycin acid sulfate, vancomycin, hydrocortisone and hydrocortisone 21-acetate, cortisone and cortisone acetate, testosterone and testosterone propionate, testosterone-17-hemisuccinate, thrombin, and lidocaine-HCl solution as used for local anesthesia as well as many other drugs or any compound which is desired to be incorporated for sustained release.

The silicic acid compounds useful in the practice of the invention include those alkyl ortho silicate monomers and prepolymers which hydrolyze to form a corresponding alkyl alcohol and a silica polymer, and include the tetraethyl ester of silica acid which, on hydrolysis and gelation, provides for the release of ethanol, a nontoxic compound. Other lower alkyl esters or ortho silicate may be employed, such as methyl or propyl esters; however, these compounds may be employed only where the corresponding by-products are acceptable for use, so the preferred compound is the tetraethyl ortho silicate monomer or prepolymer. The amount of the silicate in the composition may vary, but typically comprises up to about 50% by weight; for example, from about 5% to 35% by weight, and more particularly 10% to 30% by weight. The ortho silicate may be prepolymerized partly, in order to decrease the gelation time when topically applied, such as, for example, up to 50% prepolymerization, provided that the resulting composition is still of sufficiently low viscosity, so that the solution may be applied topically as a liquid prior to gelation.

In the preparation of a self-gelling composition suitable for use in the oral cavity, the active ingredient may be one or more water-soluble, fluoride-containing compounds, and more particularly preferred are ammonium fluoride compounds, although other compounds, such as sodium, potassium, fluoride, alone or in combination with ammonium fluoride and other suitable fluoride compounds, or in combination with other reagents, such as phosphates or monofluorophosphates, may be employed. Typically, the amount of the fluoride compound is sufficient to prevent or to inhibit dental caries, and more particularly usually ranges from 0.01 moles to 1.5 moles; for example, 0.5 to 1.2 moles, but can be effectively lowered to concentrations below 1000 ppm F, and more particularly from 10–500 ppm F, for example, 200 ppm f, if imidazole-HCl type of a compound is also used as a gelling facilitating agent. Where the active ingredient comprises a drug, such as an antibacterial agent like chlorhexidine, or an antibiotic like tetracycline or erythromycin, the amount of the drug is sufficient to prevent infection or to treat the condition for which it is applied and for the time period desired, such as an amount of 0.05% to 20% by weight; for example.

A gelling facilitating agent is employed to control gelling time. In order to provide working time for the mixing and application of the preparation, the apparent gelation; that is, conversion to the gel state, should be initiated at a certain time after the reaction has been started. The gelling time should be less than 24 hours and more typically, for the self-gelling composition, less than about 1 hour after application; for example, 30 minutes, and preferably with the use of the accelerator compounds, less than about 10 minutes after application. The gelation should be completed substantially within a desired, predetermined gel time, such as about 2 to 3 minutes.

The amount and nature of the gelling facilitating agent are selected to provide the desired gelation time, and may vary, depending on the materials and amounts used. Typically, and, for example, where surface-active agents are used as the gelling facilitating agent, the amount may range from 0.001% to 5% by weight; for example, 0.01% to 1%. The gelling facilitating agent may comprise a fluoride ion, an ammonium ion, imidazole-HCl or a surface-active agent, alone or in combination. Thus, in self-gelling, dental-caries-preventing compositions, the ammonium fluoride may serve as an active ingredient and as the gelling facilitating agent where a fluoride compound and a separate ammonium compound are used, the concentration of the ammonium compound may range in the same or different concentration as the fluoride compound.

Surface-active agents may be used alone or with other gelling facilitating agents, and such surface-active agents would include, but not be limited to: pyridinium compounds, such as cetyl pyridinium bromide and chloride; alkali and ammonium salts of fatty-acid sulfates, such as the sodium salts of lauryl sulfate or sarcosinates; and nonionic surface-active agents, such as the polyoxyethylene derivatives of fatty-acid partial esters of sorbitol anhydrides known as Tween surfactants (a trademark of ICI United States, Inc.), or combinations thereof, and the nonionic polyoxyethylene derivatives of fatty alcohols, such as lauryl and myristyl alcohols, known as Tergitols (a trademark of the Union Carbide Corp.).

A variety of buffering agents may be employed in the composition to provide a buffered pH, which include, but are not limited to, the weak acid salts, such as acetates, tartarates, such as the water-soluble salts of phosphoric acid, citric acid, tartaric acid, lactic acid, acetic acid and the like. These agents are employed in minor amounts; for example, 0.1% to 4% by weight of the composition, to provide a buffer and to maintain the pH of the composition. Typically, the pH of the aqueous solution may range from about pH 3 to as high as pH 8.5, but more typically ranges from about 4 to 7.5.

Other additive ingredients may be incorporated into the composition, such as viscosity-thickening, viscosity-enhancing, and control agents, oils, flavoring and sweetening agents, coloring agents, stabilizers, solid particulate filler and inert materials, humectants, glycols like glycerol, and the like.

Viscosity modifying agents would include; for example, PVP, carboxymethylcellulose and hydroxypropylcellulose. The self-gelling composition may be prepared as solutions, emulsions, ointments and creams for cosmetic and dermatological use. The viscosity modifying agents and the glycols are generally used in an amount up to about 10 weight percent or 0.1 to 5 weight percent.

In use, the ingredients of the composition are combined by a vigorous mixing action, typically with a mechanical mixer, such as a static mixer, just prior to use, by the applicator, such as a dentist or hygienist. Typically, a solution containing the active ingredients, such as a fluoride or drug, and the gelling ingredient, such as a silicate monomer or polymer, is admixed with a solution containing the gelling facilitating agent and accelerator compound. After mixing, the resulting low-viscosity emulsion is topically applied usually at least several minutes before the gel time, so that the liquid will be distributed and will penetrate the desired area prior to gelling. The gelling time is defined as the period of time from the beginning of the mixing until the formation of a completely nonpourable, semirigid gel phase or state.

The invention will be described for the purpose of illustration only in connection with particular examples; however, it is recognized that various changes, modifications and improvements may be made by those persons skilled in the art, all falling within the spirit and scope of the invention.

DESCRIPTION OF THE EMBODIMENTS

EXAMPLE 1

In the past, in order to achieve a conversion from a liquid to a gel state within a few minutes time, a relatively high concentration of a fluoride solution as a gelation agent with or without a surface-active agent was employed. For example, a self-gelling composition was prepared with vigorous mixing of 20% by weight of tetraethoxysilane (TES or ethyl orthosilicate) as a neutral solution with sodium lauryl sulfate (SLS) or cetyl pyridinium chloride (CPC) as a surface-active agent with an increasing concentration of NaF or $NH_4F$ with the gelation time noted with the following results of Table 1.

TABLE 1

| NaF (M) | Surfactant (0.03 M) | Gelation Time |
|---|---|---|
| 1.0 | none | 24 h |
| 1.0 | CPC | 2 min 20 s |
| 0.5 | CPC | 2 min 50 s |
| 0.2 | CPC | 3 min 40 s |
| 0.05 | CPC | 11 h |
| NH.F (M) | Surfactant (0.03 M) | Gelation Time |
| 1.0 | none | 2 min 40 s |
| 1.0 | SLS | 1 min 15 s |
| 0.5 | SLS | 2 min 40 s |
| 0.2 | SLS | 8 min 30 s |
| 0.05 | SLS | 2 h |

To achieve gel conversion in minutes, sodium fluoride had to be present in 0.2 M or more concentration, while ammonium fluoride in the 0.5–1 M range did not require the presence of a surfactant to achieve gelation. In the presence of SLS the fluoride concentration could be lowered to the 0.2 M range.

EXAMPLE 2

The addition of other quaternary ammonium surface-active agents with varying carbon chain lengths of $C_{12}$–$C_{16}$ to the sodium fluoride compositions was carried out with the results shown in Table 2.

TABLE 2

| 20% TES; neutral 0.75 M NaF | |
|---|---|
| Surface Active Agent (0.03 M) | Gelation Time |
| cetylpyridinium-Cl | 2 min 30 sec |
| cetyldimethylethylammonium-Br | 2 min 50 sec |
| cetyltrimethylammonium-Br | 2 min 50 sec |
| hexadecyltrimethylammonium-Br | 2 min 50 sec |
| tetradecyltrimethylammonium-Br | 4 min 30 sec |
| dodecyltrimethylammonium-Br | 6 h |

The data of Table 2 indicates that increasing the length of the chains decreases the gelation time and the replacement of an aliphatic chain for the aromatic pyridinium radical shortens the gelation time.

EXAMPLE 3

A high concentrated NaF, 20% TES solution was then tested for gelation time with the addition of 1% by weight of imidazole-HCl in the 5–9 pH rnage with the results shown in Table 3.

TABLE 3

| 20% TES, 0.75 M NaF, 1% imidazole-HCl | |
|---|---|
| pH | Gelation Time |
| 9 | 4 min 15 sec |
| 8 | 1 min 25 sec |
| 7 | 1 min 10 sec |
| 6 | 1 min 20 sec |
| 5 | 1 min 50 sec |

The data of Table 3 shows short gelation time with a high concentration of fluoride.

EXAMPLE 4

Additional tests were conducted employing imidazole-HCl as an accelerating agent in a neutral fluoride TES solution using a low decreasing concentration of fluoride with a surface-active agent, Tergitol 15-S-12 with the results shown in Table 4.

TABLE 4

| 20% TES, 1% imidazole-HCl, 1% Tergitol 15-S-12, neutral NaF solution | |
|---|---|
| F conc. (ppm) | Gelation Time |
| 1000 | 1 min 20 sec |
| 500 | 1 min 45 sec |
| 250 | 2 min 45 sec |
| 100 | 5 min |
| 50 | 18 min |
| 10 | 24 h |

The surface-active agent Tergitol is a nonionic surfactant based on polyoxyethylene derivatives of fatty alcohols, such as lauryl and myristyl alcohols. The data illustrates short gelation times of 5 minutes or less with more than 100 ppm of fluoride in combination with the Tergitol and the imidazole-HCl.

EXAMPLE 5

Additional tests were carried out in which this amount of imidazole-HCl was varied and the change in gelation time noted with the results shown in Table 5.

TABLE 5

| 250 ppm F (NaF, pH 7), 20% TES, 1% Tergitol 15-S-12 | |
|---|---|
| 2 | 1 min 20 sec |
| 1 | 2 min 45 sec |
| 0.5 | 3 min 30 sec |
| 0.25 | 4 min 45 sec |
| 0.1 | 45 min |

As illustrated by the data, the 2% imidazole concentration provided a 100% conversion into a gel in 1 min 20 sec, while the 0.25% concentration brought the gelation time to 4 min and 45 sec and further decrease of imidazole concentration to 0.1% resulted in about ten fold increase in the gelation time.

EXAMPLE 6

Using the 250 ppm F neutral sodium fluoride solution in a combination with 20% of TES and 1% Tergitol 15-S-12 the effect of the addition of about thirty other nitrogen-containing accelerator compounds at the 0.1 M concentration was tested, which compounds were derivatives either of imidazole or pyridine or substances structurally related to these compounds with the results shown in Table 6. Imidazole and 1-methylimidazole was about equally effective for short gelation times, indicating that tautomerism or the hydrogen of the imino group are not actively involved in the catalysis. Great fluctuations in gelation times were observed when these derivatives were tested which may point to the existence of weak bonds between substances and the substrate.

EXAMPLE 6

TABLE 6

| 20% TES + (200 ppm F (NaF), 0.1 M agent, pH 6–7 + 1% Tergitol 15-S-12 | |
|---|---|
| Agent | Gelation Time |
| 1-H imidazole | 3 min 10 sec |
| 1-methylimidazole | 3 min 35 sec |
| 4-methylimidazole | 4 min 30 sec |
| 2-methylimidazole | 7 min 25 sec |
| 4-(hydroxymethyl)imidazole | 7 min 40 sec |
| 2,4-dimethylimidazole | 2 h |
| histamine | 11 min 30 sec |
| pyrazole | 7½ h |
| pyrrole | >24 h |
| pyrrole 2-carboxaldehyde | 6 h |
| pyrrolidine | >24 h |
| 1-pyrrolidinecarboxaldehyde | 6 h |
| 2-imidazolidone | >24 h |
| 1-H—tetrazole | >24 h |
| 1, 2, 4-triazole | 6 h |
| 1H—1, 2, 4-triazole-3-thiol | 15 min |
| pyridine | 1 h 25 min |
| 2-hydroxy pyridine | 1 h 45 min |
| 3-hydroxy pyridine-N—oxide | 1 h 15 min |
| 2-pyridine carboxaldehyde | 1 h 40 min |
| pyrazine | 10 h |
| pyrazineamide | 7 h |
| pyrimidine | 7 h |
| 2-hydroxypyrimidine | 2 h |
| 4 (3H) pyrimidone | 40 min |
| purine | 1 h |
| adenosine triphosphate disodium salt | 45 min |
| triazine | 6 h |
| N—(2-amino ethyl) piperazine | 1 h |
| morpholine | 1 h |

EXAMPLE 7

The accelerator agent should be used in combination with a gelling facilitating agent, particularly a surface-active agent to achieve short gelation times as shown by the data in Table 7.

TABLE 7

| 20% TES, 500 ppm F (NaF), pH 6–7 | | |
|---|---|---|
| Agent | Surfactant (1%) | Gelation Time |
| — | CPC | >24 h |
| — | Tergitol 15-S-12 | >24 h |
| Imidazole-HCl | — | 4 h |
| Imidazole-HCl | CPC | 7 min |
| Imidazole-HCl | Tergitol 15-S-12 | 5 min |

EXAMPLE 8

The self-gelling accelerated composition may be employed for the sustained release of therapeutic agents and a self-gelling composition with an accelerator agent was tested with various selected representative common therapeutic agents as shown in Table 8. The gelation times were below 3 minutes.

TABLE 8

| 20% tetraethoxysilane, 250 ppm F, 1% imidazole-HCl, 1% Tergitol 15-S-12 ||
| --- | --- |
| Chlorhexidine | Cortisone-acetate |
|  | Cortisone |
| Tetracycline | Hydrocortisone 21-acetate |
| Penicillin V-F salt | Hydrocortisone |
| Bacitracin | Testosterone propionate |
|  | Testosterone |
| Polymyxin B-sulfate | Testosterone-17B hemisuccinate |
| Kanamycin acid sulfate |  |
| Vancomycin | Thrombin |
|  | Gamma-Globulin |
|  | Lidocaine-HCl |

The drugs were added in concentration near to their saturation points or finely dispersed in the composition. All the tested compositions of Table 8 gelled within a three minute period of time. The bacitracin, polymyxin B-sulfate, kanamycin acid sulfate in 5% concentration and 2% chlorhexidine diacetate dissolved completely in the medium, while tetracycline, 5% chlorhexidine diacetate, the penicillin tablet and vancomycin remained partially in a solid form dispersed in the gel. Addition of viscosity modifying agents like methylcellulose affected solid separation.

EXAMPLE 9

| 70 parts | water |
| --- | --- |
| 20 parts | tetraethoxy silane (= tetraethyl orthosilicate) |
| 10 parts | aminopropyl triethoxy silane (= aminopropyl, triethyl orthosilicate) |
| 1 part | sodium lauryl sulfate (surface-active agent) |
| 0.2 parts | chlorhexidine (antibacterial agent) |
| gels in 5 minutes | |

Example 9 is a self-gelling composition having an antibacterial agent suitable for veterinary use, such as the treatment of mastitis; it is done by applying or coating the affected area with the liquid. The sustained release of the antibacterial agent from the gel is identified above.

EXAMPLE 10

Examples 10 and 11 are suitable for use in the treatment of diseases of the oral cavity, particularly peridontal disease, by the topical application of the solution to periodontal pockets and areas, to provide for the sustained release of the antibiotic agent.

| 70 parts | water |
| --- | --- |
| 20 parts | tetraethoxy silane (= tetraethyl orthosilicate) |
| 10 parts | aminopropyl triethoxy silane (= aminopropyl, triethyl orthosilicate) |
| 1 part | sodium lauryl sulfate |
| 16 parts | erythromycin (antibiotic) |
| gels in 2 minutes | |

EXAMPLE 11

| 60 parts | 0.1 M ammonium dihydrogen phosphate solution |
| --- | --- |
| 20 parts | tetraethoxy silane (= tetraethyl orthosilicate) |
| 20 parts | aminopropyl triethoxy silane (= aminopropyl, triethyl orthosilicate) |
| 0.1 parts | Tween 20 (surface-active agent) |
| 3.3 parts | tetracyclin (antibiotic) |
| gels in 2 minutes | |

The accelerated self-gelling composition illustrated may be applied topically as desired to affect a sustained release of the active therapeutic agent to the body site where the in situ gelation occurs.

What is claimed is:

1. A self-gelling aqueous therapeutic gel composition for the sustained release of a therapeutic agent from the gel composition, which composition comprises:
   (a) a low-viscosity liquid aqueous emulsion of a monomer or preopolymer of alkyl orthosilicate in an amount ranging from about 5 to 50 percent by weight of the composition;
   (b) a water-soluble fluoride compound in an amount up to about 1,000 parts per million of the composition;
   (c) a surface-active agent in an amount of up to about 10 percent by weight of the composition and sufficient to provide in combination with the water-soluble fluoride compound, the in situ gelation of the low-viscosity solution on admixing from a liquid to a gel state;
   (d) a therapeutic agent other than the water-soluble fluoride compound, in an amount of up to about 20 percent by weight of the compositions, the therapeutic agent selected to treat the condition for which the composition is to be administered or applied; and
   (e) an accelerator compound to accelerate the time period between the conversion of the admix liquid composition to a gel state which comprises from about 0.01 to about 10 percent by weight of imidazole or an alkyl or hydroxyl substituted imidazole and the pharmaceutically-acceptable salts thereof.

2. The composition of claim 1 wherein the therapeutic agent is selected from a group consisting of: chlorhexidine; tetracycline; penicillin; bacitracin; polymyxin B-sulfate; kanamycin acid sulfate; vancomycin; hydrocortisone and hydrocortisone 21-acetate; cortisone and cortisone acetate; testosterone and testosterone propionate; testosterone-17B-hemisuccinate; erythromycin; thrombin; and lidocain-HCl solution as used for local anesthesia.

3. The composition of claim 1 wherein the water-soluble fluoride compound is selected from the group consisting of sodium fluoride, potassium fluoride, ammonium fluoride, and combinations thereof with mono fluorophosphates.

4. The composition of claim 1 wherein the surface-active agent is selected from a group consisting of alkali and ammonium salts of fatty acid sulfates, quaternary ammonium salts, and polyoxyethylene derivatives of fatty acids and alcohols.

5. The composition of claim 4 wherein the surface-active agent comprises a polyoxyethylene derivative of $C_{12}$–$C_{16}$ fatty alcohols.

6. The composition of claim 1 wherein the surface active agent is present in an amount of about 0.001 to 2 percent by weight of the composition.

7. The composition of claim 1 wherein the accelerator compound is present in an amount of from about 0.01 to 2 percent by weight of the composition.

8. The composition of claim 1 wherein the accelerator compound comprises a mono or di methyl or hydroxy substituted imidazole.

9. The composition of claim 1 which includes up to about 10 percent by weight of a viscosity modifying agent.

10. The composition of claim 1 wherein the water-soluble fluoride compound is present in an amount of from about 10 to 500 ppm.

11. The composition of claim 1 wherein the composition includes a buffering agent to maintain the pH of the composition from about 4 to 7.5.

12. The composition of claim 1 wherein the alkyl orthosilicate comprises a tetraethyl orthosilicate, aminopropyl triethyl orthosilicate or combinations thereof.

13. The composition of claim 1 wherein the accelerator compound comprises imidazole-HCl, 1 methyl imidazole, or 4 methyl imidazole.

14. A method for the sustained release of a therapeutic agent by the application or administration of a self-gelling composition, which method comprises:
   (a) admixing the components of the self-gelling composition of claim 1 together to form a liquid composition;
   (b) applying or administering to the patient, prior to the gelling of the composition, the admixed liquid composition; and
   (c) converting the liquid composition from a liquid to a gel state to provide a gelled composition for the sustained release of the therapeutic agent.

15. The method of claim 14 which includes converting the liquid composition in situ from a liquid to a gel state within about 3 minutes or less of the admixing of the composition.

16. The method of claim 14 which includes topically applying the self-gelling composition into the oral cavity of a patient in and about any periodontal pockets around the teeth surfaces of the patient to provide for the sustained release of a periodontal disease-effective therapeutic agent in the oral cavity.

17. The method of claim 14 wherein the therapeutic agent is selected from the group consisting of: chlorhexidine; tetracycline; penicillin; bacitracin; polymyxin B-sulfate; kanamycin acid sulfate; vancomycin; hydrocortisone and hydrocortisone 21-acetate; cortisone and cortisone acetate; testosterone and testosterone propionate; testosterone-17-B-hemisuccinate; erythromycin; thrombin; and lidocaine-HCl solution as used for local anesthesia.

18. The method of claim 15 wherein the self-gelling composition comprises about 10 to 30 percent by weight of ethyl orthosilicate and wherein the accelerator compound comprises from about 0.1 to 2 percent by weight of an imidazole or a di or mono methyl or hydroxyl substituted imidazole and the pharmaceutically-acceptable salts thereof.

19. The method of claim 14 which includes admixing the self-gelling composition at a pH of from about 4.5 to 7.5.

20. The method of claim 13 which includes topically applying the self-gelling composition to the body of a patient.

21. The method of claim 14 which includes converting the liquid composition to a gel state within about one hour of admixing.

* * * * *